United States Patent [19]
Poveromo

[11] Patent Number: 4,752,224
[45] Date of Patent: * Jun. 21, 1988

[54] DENTURE CONNECTOR

[75] Inventor: Melvin D. Poveromo, Miami, Fla.

[73] Assignees: George Poveromo; Marc Poveromo; Melanie Poveromo, all of Miami Beach, Fla.

[ * ] Notice: The portion of the term of this patent subsequent to Mar. 4, 2003 has been disclaimed.

[21] Appl. No.: 801,347

[22] Filed: Nov. 25, 1985

Related U.S. Application Data

[63] Continuation-in-part of Ser. No. 614,078, May 25, 1984.

[51] Int. Cl.[4] .............................................. A61C 13/22
[52] U.S. Cl. .................................... 433/181; 433/182
[58] Field of Search ................ 433/180, 181, 182, 183

[56] References Cited

U.S. PATENT DOCUMENTS

| | | | |
|---|---|---|---|
| 866,304 | 9/1907 | Roach | 433/183 |
| 1,297,199 | 3/1919 | McAuley | 433/181 |
| 1,297,561 | 3/1919 | Guntner | 433/181 |
| 1,324,476 | 12/1919 | Supplee | 433/181 |
| 1,520,809 | 12/1924 | Cohen | 433/181 |
| 1,693,845 | 12/1928 | Kellner et al. | 433/182 |
| 3,117,377 | 1/1964 | Poveromo | 433/182 |
| 4,196,516 | 4/1980 | Poveromo | 433/182 |
| 4,362,509 | 12/1982 | Sule | 433/181 |
| 4,573,923 | 3/1986 | Poveromo | 433/181 |

FOREIGN PATENT DOCUMENTS 8517420 9/1985 Fed. Rep. of Germany ...... 433/181

*Primary Examiner*—John J. Wilson
*Attorney, Agent, or Firm*—Sughrue, Mion, Zinn, Macpeak and Seas

[57] ABSTRACT

A denture connector is provided with a hollow cylindrical female member having a retainer plate embedded in a denture crown. A male member comprises a top planar surface having a lateral projection to which there is attached a retainer block having projecting fins on outer walls thereof. A boss depends from an undersurface of the top planar member and has a bore coextensive with a threaded recess in said undersurface of the top planar member. A threaded screw with a removable expandable sleeve thereon is threaded into the threaded recess to complete the male unit. The male unit is inserted into the female unit whereby a tolerance space exists between the outer diameter of the sleeve and the inner diameter of the female cylinder. The retainer block attached to the lateral projection has a space therein whereby the combination of space and the projector fins ensure firm embedment of the retainer block in denture material.

11 Claims, 4 Drawing Sheets

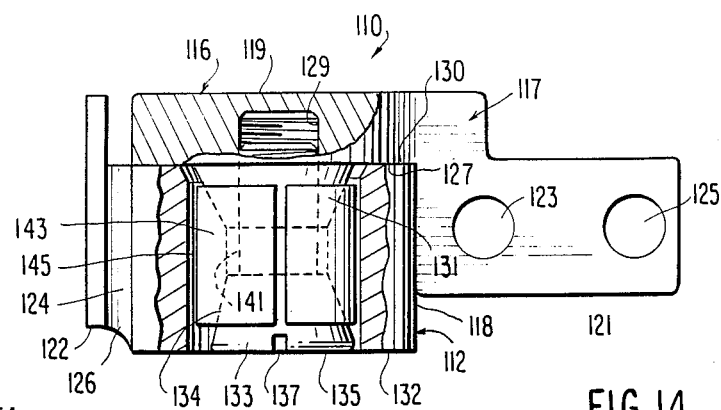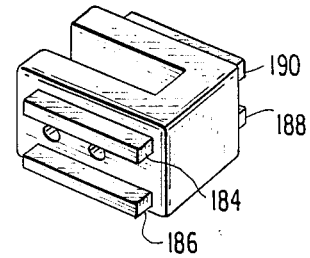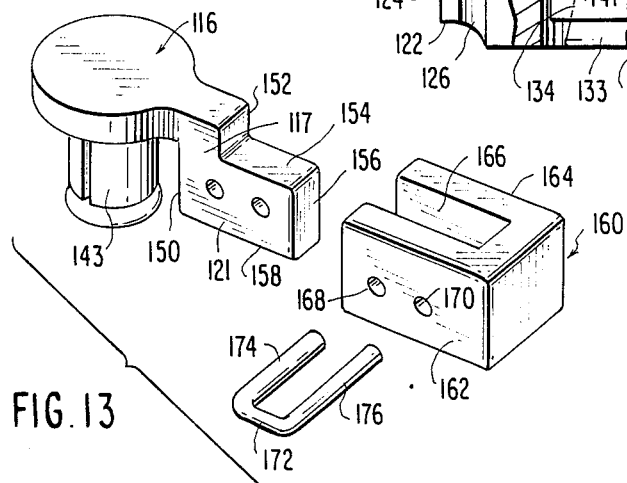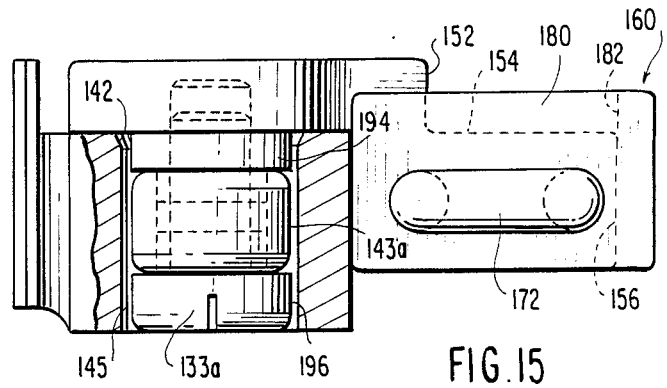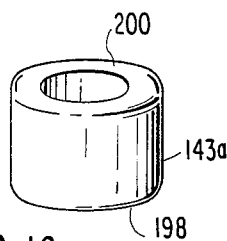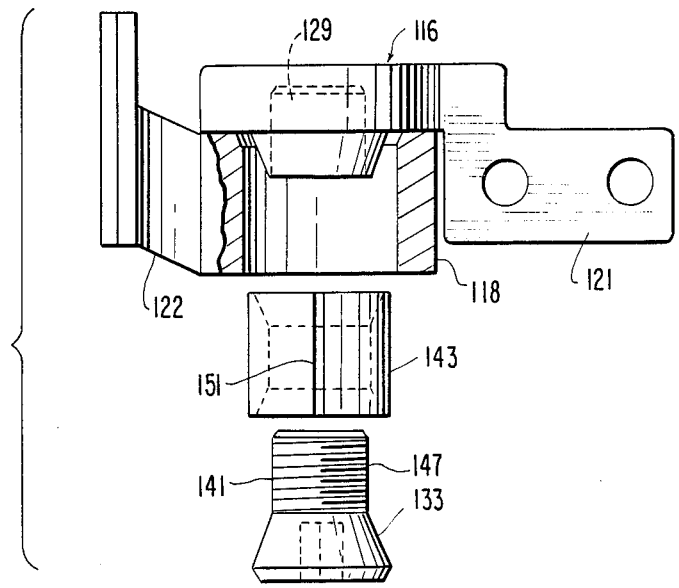

DENTURE CONNECTOR

CROSS REFERENCE

This is a continuation-in-part of application Ser. No. 614,078, filed May 25, 1984, now U.S. Pat. No. 4,573,923; the contents of which is made a part hereof by reference.

BACKGROUND OF THE INVENTION

1. Field of the Invention

This invention pertains to a connector for dentures which includes a female member, a male member and a cylindrical insert.

2. Statement of the Prior Art

The prior art shows denture connector or attachment devices comprising male and female metal members. None of these prior art devices discloses a denture attachment comprising a female member, a male member having a metal or non-metal sleeve for insertion into the female member and means for expanding the male member as wear occurs on the sleeve.

It is one object of this invention to provide a denture connector or attachment which is simple and inexpensive to construct and install.

It is a further object of this invention to provide a denture attachment or connector wherein the female member comprises a hollow cylinder having a web attached to the outer wall thereof and further having a retention plate attached to the web which plate is embedded in the crown of a tooth. The lower edge of the web has a curvature to accommodate the crest of the gingiva.

It is another object of this invention to provide a male member comprising a solid cylinder which has a flanged edge for easy insertion into the female member. The male member is provided with at least one slit in an end thereof whereby the cylinder may be compressed upon the application of pressure thereto.

Yet another object of this invention is to provide a male member with an extension shank member whereby the male member may be rotated when positioned inside the female member and whereby the male member may be attached to adjacent denture material.

It is yet another object of this invention to provide the male member with an outer sleeve which functions as a friction and bearing surface when the male member and sleeve are positioned within the female member.

And still a further object of this invention is to provide means to expand the male member which comprises at least one slit in an end of the male member through the diameter thereof and a tapered recess to accommodate an expansion member.

And yet another object of this invention is to provide a male member in the form of a screw which is threaded into an extension shank member.

Yet still another object of this invention is to provide a male member and insert whose combined diameter is smaller than the inner diameter of the female whereby a tolerance space exists therebetween.

It is still another object of this invention to provide a male member comprising an attachment element having a shank projection from a planar surface in which there is a threaded recess to receive an end of a threaded screw. The attachment element of the male member has a connector block having projections to assist in retaining the connector to adjacent denture material.

These and other objects of this invention will become more apparent from a review of the specification when taken in light of the annexed drawings.

BRIEF DESCRIPTION OF THE DRAWINGS

FIG. 12 is a perspective view in section of a modified denture connector showing an attachment member, a sleeve and a female member with a tolerance space between the sleeve member and female member.

FIG. 13 is a perspective view of male member, sleeve and attaching screw and a retainer block with securing pin.

FIG. 14 is a perspective view of the retainer block with projections to assist in maintaining the retainer block in adjacent denture material.

FIG. 15 is a perspective view in section of the denture connector showing the connector member assembled to its support arm.

FIG. 16 is an elevated view of the sleeve which may be continuous or split.

FIG. 17 is an exploded view of the connector of FIG. 12.

DESCRIPTION OF THE PREFERRED EMBODIMENT

Figure 1:
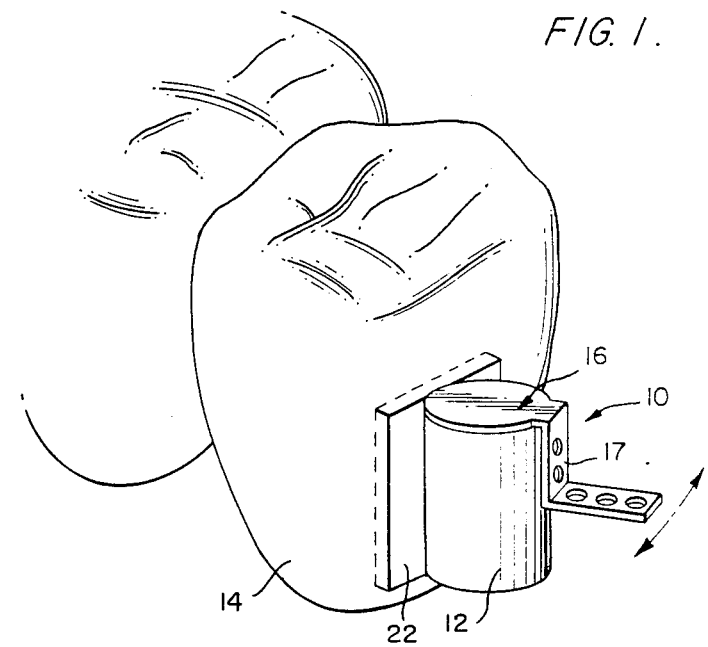
FIG. 1 is a perspective view of the invention showing a female member having a retention plate which is embedded in a crown and a male member rotatable in the female member and having a connector for attachment to adjacent denture.

Referring now in more detail to the drawings, FIG. 1 shows a denture connector 10 comprising a female member 12 attached to the crown of a denture 14 and a male member 16 having an attachment shank 17 for attaching the male member to adjacent denture area.

Figure 2:
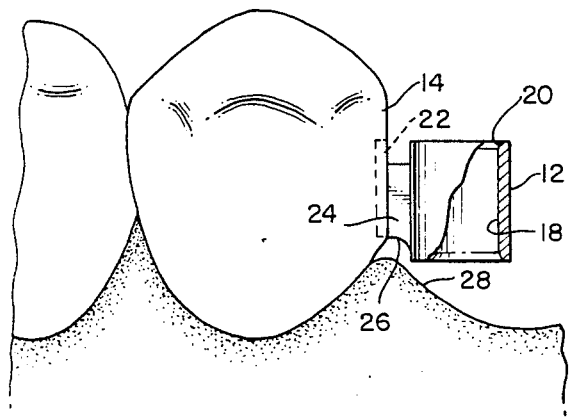
FIG. 2 is a side view of the female member which is a hollow cylinder attached to the crown by a retention plate.

The female member, FIG. 2, comprises a cylindrical portion 18 having an outwardly flared upper edge 20. The cylindrical portion 18 is attached to a denture crown 14 by a retainer plate 22 and an intermediate web portion 24. The bottom edge of the web portion 24 is curbed at 26 to accommodate the crest 28 of the gingiva which is generally elevated next to the crown.

Figure 3:
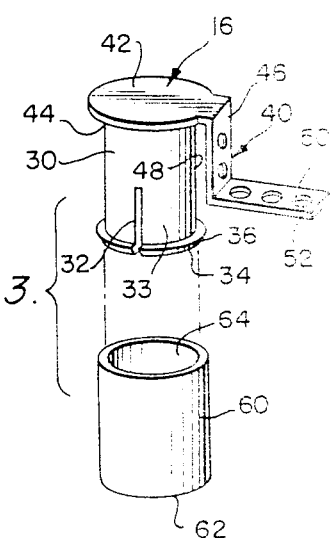
FIG. 3 is an exploded view of the male member with a laterally projecting connector arm and a cylindrical insert.

The male member 16, FIG. 3, comprises a solid cylindrical member 30 having a slit 32 extending across the diameter thereof and extending vertically approximately one half the height of the member 30. The male member has a flared bottom edge 34 and a protruding lip 36, the purposes of which will be explained below.

The male member 16 has an attachment member 40 comprising an upper planar portion 42 which is secured to the upper edge 44 of the male member 30, a vertical portion 46 distal from the outer wall 48 of the male member 30 and a lateral arm 50 in which there are a number of apertures 52. The arm 50 facilitates rotation of the male member within the female member and also facilitates attachment of the male member to the adjacent denture area. The apertures in the arm 50 receive some of the denture material thus insuring a strong bond.

Figure 4:
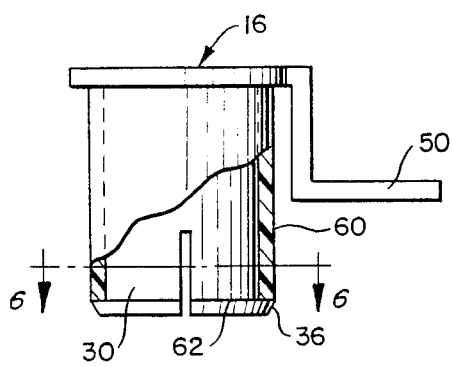
FIG. 4 is a perspective view of the male member showing the sleeve thereon.

In FIG. 4, the plastic sleeve 60 is shown as being slightly smaller in height than the height of the cylinder member 30 and also slightly smaller in inner diameter than the outer diameter of the cylinder member 30. To insert the plastic sleeve, merely compress the bottom area of the male cylinder 30 which will yield due to the slit and slip the plastic sleeve onto the cylinder 30 until the lip 36 engages the bottom edge 62 of the sleeve. Release of the male member will cause the bottom portion 33 to expand thus engaging the inner wall 64 of the sleeve 60 in a tight grip.

Figure 5:
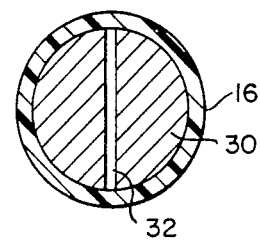
FIG. 5 shows the bottom of the male member having a slit and a sleeve over the male member.
Figure 6:
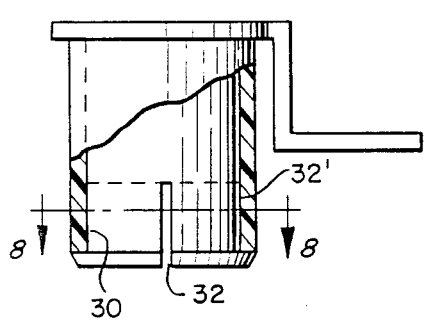
FIG. 6 is a view of the male member and the sleeve.
Figure 7:
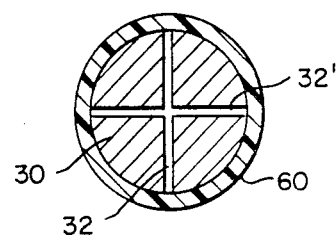
FIG. 7 shows the bottom of the male as having a double slit.

The male member 16 with the sleeve attached is then inserted into the hollow cylindrical female member 12. Insertion of the male member into the female member is made easy by the flared bottom edge 34 of the male member and the flared upper edge 20 of the female member. When the male member with the sleeve thereon is in position in the female member, the male member and sleeve are readily rotatable by manipulation of the lateral arm 50. Easy rotation of the male member within the female member is desirable so as to provide optimum positioning of the lateral arm 50 over the crest of the gingiva. FIG. 5 shows an end view of the assembled components 30 and 60 and the slit 32. FIGS. 6 and 7 show a modification in that the cylinder 30 has a double slit 32 and 32' for easy compression of the bottom of the cylinder 30.

FIG. 4 shows the plastic sleeve 60 in position on the cylinder member 30 with the lip 36 engaged against the bottom edge 62 of the plastic sleeve.

Figure 8:
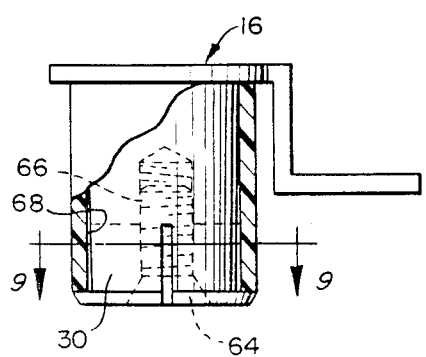
FIG. 8 is a perspective view of the male member and shows an expansion screw extended into the end thereof.
Figure 9:
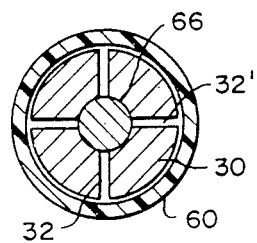
FIG. 9 is an exploded view of another embodiment of the male member, sleeve and shank connector member.

In the embodiment of FIG. 8, the male member 16 is constructed so that the cylinder 30 tapers downwardly and inwardly whereby the outer diameter of the cylinder 30 is slightly smaller than the inner diameter of the sleeve 60. When the sleeve is fitted over the male cylinder 30, a screw 64 is threaded into a recess 66 in the cylinder 30 thus expanding the male cylinder 30 against the inner wall 68 of the sleeve 60. Should the sleeve 60 become worn or loose during use, it is only necessary to continue inward rotation of the screw 64 to further expand the male cylinder 30 against the sleeve 60. When the sleeve becomes totally worn or damaged, it is removed from the male cylinder 30 and replaced by a new sleeve.

Figure 10:
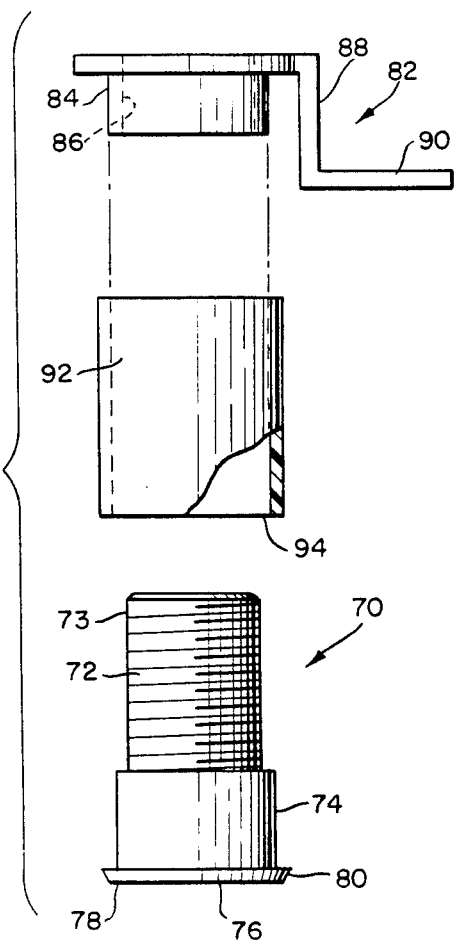
FIG. 10 is a perspective view of the assembled male member, sleeve and shank connector member.
Figure 11:
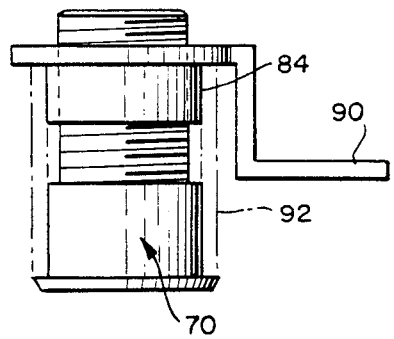
FIG. 11 is a perspective view of the assembled connection.

In FIG. 10 there is shown a modified embodiment of the invention wherein the male cylinder is a screw 70 having a threaded portion 72, a shank portion 74 and a base portion 76 having a lip 78 which is flared at 80. The attachment member 82 comprises a hollow shank portion 86 having internal threads 86 to receive the threaded end 73 of the screw 70. The connector has a vertical section 88 and a lateral arm 90 which is embedded in adjacent denture material. The nylon sleeve 92 is telescoped onto the shank portion 84. The threaded end 73 and shank 74 of the screw 70 are telescoped into the sleeve and threaded into the shank 84 until the lip 78 engages the edge 94 of the sleeve. The assembled screw 70, shank 84 and plastic sleeve 92 are shown in FIG. 11.

FIGS. 12 through 17 disclose yet another modification of the invention.

FIG. 12 shows a denture connector 110 comprising a female member 112 which is designed to be attached to the crown of a denture 14, FIG. 1, and a male unit 116 having a shank portion 117 with a lateral projection 121 which is used in conjunction with a retainer block 160, FIG. 15.

The female member 112 has a hollow cylindrical portion 118 having a retainer plate 122 which is embedded in a denture crown 14 of FIG. 1 and a web portion 124 which has a curved edge 126 to accommodate the crest of the gingiva, denoted number 28 in FIG. 2.

The male unit comprises a top member 116 having a planar surface 119, and a depending shank 117 from which there extends the lateral projection 121. There are a plurality of apertures 123 and 125 in projection 121. Opposite top planar surface 119 is another surface 127 with a threaded recess 129. Extending from the surface 127 is a conical boss 131 which has a bore therethrough in alignment with the recess 129. The conical boss 131 is adapted to be inserted into the cylindrical female portion 118. A screw 133 has a flat end 135 with a slot 137 therein for receiving the blade of a tool. The screw 133 has an inwardly tapering wall 134 which is complementary and symmetrical with conical boss 131. The screw 133 has a shank portion 141 having a threaded end 147 for turning into the threaded recess 129. An expandable split sleeve 143 is positioned about the shank 141 of the screw and serves to fasten the male unit in the cylindrical female member. It will be seen that the assemblage of female and male units, before expanding the sleeve, will result in a tolerance space 145 between the inner diameter of the female member and the outer diameter of the sleeve. This tolerance space may be in the dimension of between 0.1 mm and 0.4 mm. The tolerance space is important to permit ease of movement of the male unit in the female portion whereby optimum adjustment of the denture connector may be achieved.

In FIG. 13 there is shown the male unit 116 having the shank 117 having a vertical inner wall 150, which extends vertically adjacent the female member's cylindrical portion 118 and beyond the midpoint of the length thereof when the male unit 116 is completely inserted in the female member 112 as best seen in FIGS. 12 and 15, and an outer smaller dimensioned wall 152 which adjoins a top wall 154 of the lateral projection 121. The lateral projection 121 has an end wall 156 and a bottom wall 158. A removable retainer block 160 is shown to have parallel walls 162 and 164 defining a slot 166. The slot 166 receives the lateral projection 121. Retainer block 160 has a plurality of apertures 168 and 170 which align with apertures 123 and 125 in the lateral projection 121. A U-shaped pin 172 having parallel legs 174 and 176 extends through the apertures 168, 170 and 123, 125 to retain the retainer block 160 on the lateral projection 121. Upon assemblage of 121 and 160, there will be a hollow space 180 defined by wall 152, 154, side walls 162 and 164 and inside wall 182 as best seen in FIG. 15.

Retainer block member 160, FIG. 14, is provided with spaced parallel projection fins 184 and 186 on one wall 162 and projection fins 188 and 190 on the other wall 164. The fins may be integral with the retainer block member 160 or they may form separate pieces secured to the block 160 by suitable bonding means.

FIG. 15 is a slightly modified form of the structure of FIG. 12 wherein the upper edge of the cylindrical female member 118 is beveled at 142, the projection boss 194 is cylindrical and the screw 133a has generally vertical walls 196. Again, it will be seen that there is a tolerance space 145 between the sleeve 143a and the inner diameter of the cylindrical female member.

FIG. 16 shows the sleeve 143a as being a continuous hollow cylinder with slightly rounded upper and lower edges 198 and 200. It will be appreciated that the edges 198 and 200 may be dimensioned, such as in the form of the beveled edges, and that they respectively abut the cylindrical boss 194 and the flat inner surface of the screwhead formed by the straight wall of the screw 133a, FIG. 15. They may be metal or plastic or other material.

FIG. 17 shows an exploded view of the components of the structure of FIG. 12 wherein 116 is the male unit with expandable sleeve 143 having a slot or slit 151 therein and screw 133.

In operation, of the embodiment of FIGS. 12, 13 and 17, the female retainer plate 122 is embedded in a denture crown 14. The male unit 116 including the screw and sleeve is inserted into the female cylindrical portion 118 so that the inner wall 150 of the male unit's shank 117 extends adjacent to, and beyond the midpoint of the length of, the portion 118, as best seen in FIGS. 12 and 15. The screw 133 with the sleeve 143 thereon is threaded into the recess 129 until the sleeve abuts the slanted edge of the boss and the slanted edge of the head of the screw. At this position, there will be a tolerance space of between 0.1 mm and 0.4 mm between the inner diameter of the female portion and the outer diameter of the sleeve. The retainer block 160 is fitted to the lateral projection 121 by the pin 172 and the combination is then embedded in adjacent denture material. Denture material, as will be appreciated, will flow about fins 184, 186, 188 and 190 and into the space 180 thus ensuring optimum retention in the denture material. The screw 133 is then turned into recess 129, thereby expanding the sleeve 143 against the cylindrical wall of the female member. Crown 14 and the adjacent denture material are now firmly connected. Some wear will occur on the sleeve after a period of use. It is only necessary to turn the screw 133 further into the recess 129 thus continuing the expansion of the sleeve against the wall of the cylindrical female member. When the sleeve becomes completely worn, a new one is replaced. The operation of the embodiment of FIGS. 15 and 16 is similar in that, when the screw 133a is threaded into the cylindrical boss 194, the continuous sleeve 143a expands radially under the axial compressive force applied by the advancing screw.

While the invention has been described in detail with respect to a preferred embodiment thereof, it will be appreciated by those skilled in the art to which the invention pertains that numerous changes may be made in the invention without departing from the spirit and scope thereof.

What I claim is:

1. A denture connector comprising:
  a female member adopted to be attached to a denture crown;
  a male member removably received in the female member for rotation therein, said male member comprising a dependent boss and a screw,
  an expandable sleeve on the male member for securing the male member to the female member;
  a tolerance space of between 0.1 mm and 0.4 mm between the outer diameter of the sleeve and the inner diameter of the female member for permitting adjustment of the male member within the female member in the unexpanded state of said sleeve; and
  a retainer block extending from the male member for attaching the male member to adjacent denture material.

2. A denture connector according to claim 1, wherein:
  the female member comprises a hollow cylinder having flat upper and lower walls, an exposed web portion on the outer wall of the hollow cylinder and having a curved lower edge to accommodate the crest of the gingiva, and a retainer plate on the web portion for embedding in a denture crown.

3. A denture connector according to claim 1, wherein:
  said male member comprises a top planar surface, a depending shank with a laterally extending projection having apertures therein, and a threaded recess in a lower face of said top planar member; said depending boss having a bore coextensive with the recess, said screw having a threaded shank for rotation into said threaded recess, said expandable sleeve surrounding the shank of the screw, said retainer block being secured to the lateral projection, and said retainer block and said lateral projection being adapted for embedding in adjacent denture material.

4. A denture connector according to claim 3, wherein:
  said connector block comprises parallel walls defining a slot therebetween for receiving the lateral projection, apertures in at least one of said parallel walls aligned with said apertures in said lateral projection, and a U-shaped pin with parallel legs for insertion through the apertures in the retainer block and the apertures in the lateral projection for securing the retainer block to the lateral projection.

5. A denture connector according to claim 4, and:
  said retainer block having only two parallel projecting fins on each of said parallel walls for receiving denture material, the secured lateral projection and the parallel walls of said retainer block defining a slot to receive denture material whereby the lateral projection and the retainer block are firmly secured in denture material.

6. A denture connector according to claim 3 or 5, wherein:
  said boss is conical and said screw has a tapered wall, complementary and symmetrical with said conical boss, and said sleeve is split and has upper and lower tapered edges for respectively abutting said conical boss and said tapered edges of said screw.

7. A denture connector according to claim 3 or 5, and wherein:
  said expandable sleeve is plastic and has a continuous wall;
  said boss has a cylindrical wall;
  said screw has a cylindrical wall forming a screwhead; and
  said sleeve has flat upper and lower surfaces respectively abutting a flat surface on said cylindrical boss and a flat surface on said screwhead, whereby threading of said screw into said threaded recess causes axial compression and radial expansion of said plastic sleeve.

8. A denture connector according to claim 3, wherein said female member comprises a hollow cylinder having an outer wall, and wherein said depending shank has an inner wall which extends adjacent to, and beyond the midpoint of the length of, said outer wall when said male member is received in said female member.

9. A denture connector according to claim 1, and: said sleeve expandable against the cylindrical wall of the female member thus securing said male member securely within such female member.

10. A denture connector according to claim 1, wherein:
said female member has a beveled upper edge a distance from said boss defining a slot therebetween and said sleeve has a beveled upper edge defining a wedge-shaped portion for reception into said slot upon rotation of said screw to expand said sleeve.

11. A denture connector according to claim 1 and: said tolerance space is 0.3 mm.

* * * * *